United States Patent [19]

Bochner

[11] 4,129,483

[45] Dec. 12, 1978

[54] DEVICE, COMPOSITION AND METHOD FOR IDENTIFYING MICROORGANISMS

[76] Inventor: Barry R. Bochner, 1546 Arch St., Berkeley, Calif. 94708

[21] Appl. No.: 773,879

[22] Filed: Mar. 3, 1977

[51] Int. Cl.$^2$ ............................................. C12K 1/10
[52] U.S. Cl. ............................ 195/100; 195/103.5 M; 195/140; 195/127
[58] Field of Search ........ 195/139, 103.5 M, 103.5 K, 195/103.5 R, 100, 99, 101, 102, 127, 140

[56] References Cited

U.S. PATENT DOCUMENTS

| | | | |
|---|---|---|---|
| 2,871,168 | 1/1959 | Salisbury, Jr. | 195/139 |
| 3,107,204 | 10/1963 | Brown et al. | 195/139 X |
| 3,415,718 | 12/1968 | Forkman et al. | 195/103.5 M |
| 3,597,321 | 8/1971 | Kronish et al. | 195/103.5 M |
| 3,728,228 | 4/1973 | Durantz | 195/139 X |
| 3,776,818 | 12/1973 | Khan | 195/139 |
| 3,832,288 | 8/1974 | Rollender et al. | 195/103.5 M |
| 3,881,993 | 5/1975 | Freake et al. | 195/103.5 M |

*Primary Examiner*—Alvin E. Tanenholtz
*Assistant Examiner*—Robert J. Warden
*Attorney, Agent, or Firm*—Reising, Ethington, Barnard, Perry & Brooks

[57] ABSTRACT

In accordance with the invention there is provided means for identifying or testing a microorganism by growing a culture of the microorganism in contact with a composition containing: (1) an oxidation-reduction indicator, preferably a tetrazolium compound that undergoes a change in color upon reduction to a formazan compound; (2) a biodegradable compound which when catabolized by the microorganism will engender a reduction of the tetrazolium compound to the formazan compound; (3) a buffer to maintain the pH of the mixture at a level which enables culture growth without itself either engendering or preventing reduction of the tetrazolium compound to the formazan compound; and (4) a nutrient for the microorganism in a concentration sufficient to support culture growth without itself engendering reduction of the tetrazolium compound to the formazan compound. Further in accordance with the invention, there is provided a compartmentalized container to which the microorganism culture is admitted, each compartment thereof containing a composition as described but with the composition in each compartment differing from the others by way of the second-mentioned compound included. The color changes, or lack of color changes, in the various compartments are indicative of the catabolic behavior of the microorganism and hence of the type of microorganism itself.

29 Claims, 4 Drawing Figures

DEVICE, COMPOSITION AND METHOD FOR IDENTIFYING MICROORGANISMS

The subject matter of the present invention is a method, composition and device for testing or identifying microorganisms by way of a colorimetric change in the composition brought about by reduction of a compound which constitutes one of the ingredients of the composition.

BACKGROUND OF THE INVENTION

In studies concerning taxonomic classification, genetic analysis, or the physiology of catabolism and its regulation, it is common practice to use colorimetric indicator plates to facilitate the isolation or identification of microbial strains. Conventionally, however, the color differences generated with the indicators are based on pH changes. That is, the color change that differentiates the microorganisms is based on the production or consumption of acid by the microorganisms. For this reason the method has primarily found utility in testing for microorganisms that catabolize a sugar or the like to produce acid. Hence, the utility is quite restricted in that it is not applicable to the numerous strains of microorganisms that are characterized by their ability to catabolize amino acids, fatty acids, or other types of compounds with no resultant production of acid or other cause for change in pH. Also, the colorimetric technique based on changes in pH can, in many instances, produce ambiguous results. For example, often the acidic compounds initially produced are then further oxidized thereby resulting in a gradual continued change in the pH and causing the color to fade. Further, since the change in color is predicated solely on change in pH and since the change in pH caused by the microorganisms is often only slight, the technique is satisfactory only where the total chemistry of the system is such that no changes in the pH can occur other than by way of the metabolic behavior of the microorganisms.

Briefly, what I have discovered is that a far more easily controlled, more sensitive, and less restrictive way to test and identify microorganisms is feasible by a composition wherein the change in color is predicated not on a change in pH and the presence of a pH indicator but rather on an oxidation-reduction reaction which involves an oxidation-reduction indicator and which results from the catabolic behavior of the particular microorganism or type of microorganism for which the test is being made. More specifically, the preferred embodiments of the present invention involve a color change by way of the reduction of a tetrazolium compound to a formazan compound. The reducing agent causing the reduction reaction is or results from one or more of the catabolites produced during the catabolism of a test substrate compound included in the composition. Further, and more specifically with respect to the preferred embodiments of the present invention, the compositions used to identify or test the microorganism or strain of microorganism include: (1) a tetrazolium compound which undergoes a change in color upon reduction to a formazan compound; (2) a test substrate compound, i.e. a biodegradable compound which, if catabolized by the microorganism, will produce a catabolite engendering reduction of the tetrazolium compound; (3) a buffer to maintain the pH of the composition at a level which enables microorganism culture growth but which does not itself cause or prevent reduction of the tetrazolium compound to the colored formazan compound; and (4) nutrient for the microorganism or strain of microorganism in a concentration sufficient to induce culture growth without itself causing or resulting in reduction of the tetrazolium compound. Any one such composition is, by way of the particular test substrate compound it includes, useful for the colorimetric testing of a given microorganism or strain of microorganism. However, by using a series of such compositions, each with a different test substrate compound, a culture can be tested so as to identify the microorganism strain in the culture, this by way of the presence or absence of color changes in the various compositions in which the culture is allowed to grow. Hence, the invention further comprehends a test plate, or container, having separate recesses or compartments each of which contains a different such composition such that when a culture of unknown microorganism content is grown while in contact with each of the various compositions, there is indication of the particular microorganisms or microorganism strain in the culture by way of change in color or absence of change in color in the various compositions. The compositions can additionally contain some agar or the like to provide a gel or gel-like consistency for convenient growth of the microorganism cultures on the surface of the compositions.

Other details, features and advantages of the invention will appear more clearly from the following detailed description of preferred embodiments thereof made, in part, with reference to the drawings in which.

THE OXIDATION-REDUCTION COLORIMETRIC INDICATOR

Figure 1:
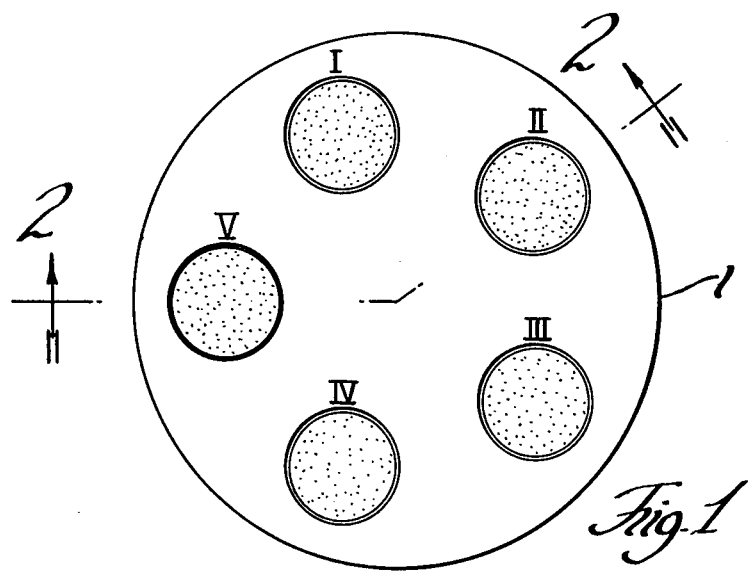
FIG. 1 is a top view of a test plate embodying the invention and useful for the convenient testing of a microorganism culture to indicate the particular microorganisms or strains of microorganisms present in the culture.

The oxidation-reduction colorimetric indicator included in the composition is a non-biodegradable compound that is substantially irreversibly reduced, with accompanying change in color, as a result of one or more of the catabolites produced by the microbial catabolism of the test substrate compound included in the composition. The preferred compounds for use as the colorimetric indicator are the tetrazolium compounds which are irreversibly reduced to form formazan with accompanying marked change in color. The tetrazolium compound used must, of course, be water soluble. The preferred tetrazolium compound is triphenyl tetrazolium chloride, i.e., 2,3,5-triphenyl tetrazolium chloride. The reduction reaction of the triphenyl tetrazolium chloride to the formazan compound is as follows:

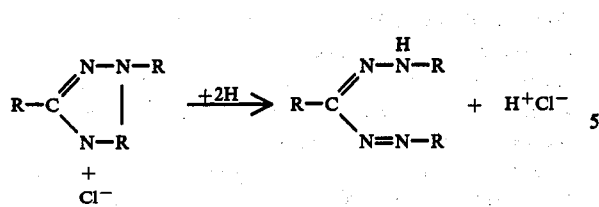

where R is a phenyl group. The triphenyl tetrazolium chloride is substantially colorless and the formazan compound precipitates out as red crystals. Hence, the reduction reaction is essentially irreversible. Other tetrazolium compounds satisfactory for the practice of the invention are exemplified by the following:

Tetrazolium violet, i.e. 2,5-diphenyl-3-a-napthyl tetrazolium chloride;
Neotetrazolium, i.e. 3,3'(4,4'-diphenylene)-bis(2,5-diphenyl) ditetrazolium chloride;
Blue Tetrazolium, i.e. 3,3'(4,4'-di-o-anisylene)-bis(2,5-diphenyl) ditetrazolium chloride;
Nitro Blue Tetrazolium, i.e. 3,3'(4,4'-di-o-anisylene)-2,2'-di(p-nitrophenyl)-bis (5-phenyl).

The concentration of the tetrazolium compound in the composition need not and preferably should not exceed about 0.1% by weight since with higher concentrations there can be inhibition of the microorganism culture growth. At the same time it is preferred that the concentration of the tetrazolium compound in the composition be at least about 0.0001% by weight since at lower concentrations the coloration resulting from the formation of the formazan compound upon reduction is too slight. Where triphenyl tetrazolium chloride is used a concentration of 0.0025% is ideal in most instances.

THE TEST SUBSTRATE

Before discussing the compounds which can be used as the test substrate it should be appreciated that the invention has utility not only for identifying the microorganism or type of microorganism present in a culture of unknown microorganism content, but also for studying and establishing the catabolic behavior of microorganisms of known identity. In the latter, cultures of the microorganism of known identity are tested with each of various compositions of the present invention, each composition containing a different test substrate, the results of each such test indicating whether the particular microorganism being tested does or does not catabolize the test substrate in the composition used for the test. By the use of a wide variety of test substrates the precise catabolic behavior of the microorganism can be established. The information so gained, along with all already-known information with respect to the catabolic behavior of the numerous and various microorganism strains, is, of course, useful for the practice of the invention for identifying the particular microorganism or type of microorganism present in a culture of unknown miroorganism content. An example of such a culture is one grown from a sample drawn from a human patient, the purpose of the test being to identify the particular microorganism in the sample as an assist to the physician in treating the patient.

Hence, the test substrate included in the composition can be any of a variety of biodegradable compounds (i.e. catabolized by one or more microorganisms or strains of microorganisms), the catabolite or catabolites resulting from the catabolism being such as to engender the reduction of the tetrazolium compound to a formazan compound with the accompanying change in color. To exemplify, the compound used as the test substrate can be selected from: the carbohydrates, including the sugars, both the monosaccharides and the polysaccharides, the starches and the celluloses; the long and short chain fatty acids as well as the other aliphatic acids, both monocarboxylic and polycarboxylic, and their salts and glycerides; the monohydric and polyhydric alcohols; the aliphatic aldehydes and ketones; the amino acids and the peptides; the aromatic compounds such as the purines, pyrimidines, ribonucleosides, benzoates, and catechols. The following specific compounds which have been used as the test substrate in the practice of the invention will serve to further illustrate: Maltose, D-glucose, L-fucose, D-ribose, lactose, D-fucose, ribitol, fumaric acid and salts, oleic acid and salts, propionic acid and salts, L-alanine, D and L-serine, L-proline, L-glycine, hydroxy-L-proline, L-valine, L-lysine, L-histidine, L-arginine, D-mannitol, D-gluconolactone, D-glucose-6-P, L-rhamnose, i-inositol, D-xylose, glycerol, lactic acid and salts, citric acid and salts, succinic acid and salts, maleic acid and salts, acetic acid and salts, butyric acid and salts, glutamic acid and salts, aspartic acid and salts, gluconic acid and salts, caproic acid and salts and glycerides, gentisic acid and m-hydroxy benzoic acid.

As indicated previously, the conventional colorimetric techniques used to test for microorganisms are dependent on pH changes and hence are generally useful only where the microorganism catabolizes sugar or other carbohydrate to generate acid. As distinguished from this, the compositions and methods of the present invention are useful not only as regards such microorganisms but also for identification or testing of microorganisms that catabolize other classes of organic compounds as illustrated by the above classes and specific examples of test substrates useful for the practice of the invention. The appropriate choice of a test substrate will be further illustrated by the specific example which will be given hereinafter.

It is preferred that the concentration of the compound used as the test substrate be at least about 2 millimols per liter, and the concentration used can range up to as high as 500 millimols per liter. The precise concentration used within this range determines the rate and extent of formazan formation and hence the rate and depth of color formation. In general, the higher the concentration of the test substrate compound the more rapid the color formation and the greater the depth of the color. However, there is seldom, if ever, need for a concentration of more than about 50 millimols per liter and a typical and preferred concentration for the test substrate compound is about 20 millimols per liter.

THE BUFFER

A buffer is included in the composition with two considerations in mind: (1) the buffer acts to maintain the pH of the composition so as to provide an environment suitable for good growth and prolonged viability of the microorganism; and (2) the buffer controls the pH of the composition so as to prevent excess alkali accumulation (which can itself cause colored formazan formation) or excess acid accumulation (which can prevent colored formazan formation). Taking into account both of these factors, the choice and concentration of the buffer generally should be such as to maintain the pH of the composition at from about 4.5 to 12.5, it being understood that the precise choice of pH to be maintained will depend on the particular tetrazolium compound being used and on the characteristics of the microorganism being tested. In general, a concentration of from about 50 to 500 millimoles per liter buffer is satisfactory.

In addition, it is important that the buffer selected should not contain compounds that the microorganisms being tested can catabolize; otherwise the buffer itself could engender reduction of the tetrazolium compound, thereby interfering with the test. Suitable for use as buffers are morpholino propane sulfonate, which is excellent, and the water soluble alkali metal and alkaline earth metal phosphates, carbonates and bicarbonates.

THE NUTRIENT

Just as in the case of the choice of the compound used as the test substrate, so also in the case of the nutrient, the precise choice must be predicated on the particular microorganism or strain of microorganism involved. Actually, the ideal nutrient would be one that supports rapid growth of all microorganisms; however, at present no such universally acceptable nutrient is known. Hence, as has been indicated, the choice of nutrient may vary from one composition to another, depending upon the microorganism or strain of microorganism for which the composition is intended. But as is well known by those skilled in the art, irrespective of the particular microorganism or strain of microorganism involved, it is always preferable, if not essential, that the nutrient include one or more compounds from each of the following groups: (1) sufficient amounts of the essential minerals for culture growth in utilizable form, for example, phosphate, sulfate, ammonia, potassium, sodium, calcium, iron, magnesium, manganese, and molybdenum; (2) amino acids including at least the twenty that are found in protein; (3) the purines and pyrimidines; and (4) the vitamins such as thiamin, biotin, pyridoxine, nicotinic acid, riboflavin, etc.

Other compounds that may be helpful to include are: unusual amino acids and amino acid-derivatives (e.g. D-amino acids, α-amino butyrate, β-alanine, taurine), peptides, gluthathione, mono- and polysaccharides, phosphorylated and aminated sugars, fatty acids, lipids, phospholipids, lecithins, polyamines, polyphosphates, ribo- and deoxyribonucleosides and nucleotides, carboxylic acids, alcohols, hemin, and quinones.

As is well known by those skilled in the art, nutrients which are close to the ideal, i.e. which are useful for a very wide range of microorganisms, are available on the market, examples being Proteose Peptone (useful, for example, at 0.2% by weight) and Tryptone (useful, for example, at 0.125% by weight) available from Difco, Inc. of Detroit, Mich. The following specific example is typical of the composition of a nutrient satisfactory for the practice of the present invention:

EXAMPLE OF NUTRIENT COMPOSITION OF BROAD APPLICABILITY

An aqueous solution containing: (a) 0.1 millimol per liter of each of the following L-amino acids or salts thereof: alanine, arginine hydrochloride, potassium aspartate, asparagine, cysteine hydrochloride, sodium glutamate, glutamine, glycine, histidine hydrochloride, isoleucine, leucine, lysine hydrochloride, methionine, phenylalanine, proline, serine, threonine, tryptophan, tyrosine, and valine; (b) 0.1 millimol per liter of each of the following purines and pyrimidines: adenine, guanine, uracil, cytosine, and thymine; (c) 0.01 millimol per liter of each of the essential vitamins as aforesaid; and (d) trace amounts of the minerals as aforesaid. Just the ordinary mineral contamination of the water and other ingredients used is generally sufficient to provide the mineral content required, except possibly for phosphate, sulfate, ammonia, potassium and magnesium, and to assure ample supply thereof the nutrient can include 0.1% by weight of each of potassium phosphate, magnesium sulfate and ammonium chloride. (The minerals can be supplied in whole or in part as the cation or anion of the buffer which is used.)

It is important to the practice of the present invention that the concentration of nutrient be low—sufficiently low that no one catabolizable organic ingredient of the nutrient be present in an amount of more than about 1 millimol per liter, and preferably about 0.1 millimol per liter. The importance of using a very low concentration of nutrient will be apparent from the fact that whereas the ideal nutrient would contain only ingredients totally assimilated by the microorganism, as a practical matter one or more of the ingredients of the nutrient will be such as can be catabolized by the microorganism. Hence, if the concentration of any such ingredient of the nutrient were high then the catabolism thereof by the microorganism would result in sufficient generation of catabolites as to falsify the test results by causing reduction of the tetrazolium compound albeit the particular microorganism could not catabolize the test substrate compound included in the composition. By maintaining the concentration of nutrient sufficiently low that no one catabolizable ingredient of the nutrient is present in an amount of more than 1 millimol per liter, and preferably about 0.1 millimol per liter, there is assurance that even though the nutrient ingredient is catabolized the amount of catabolite generated will not be sufficient to influence the test results. In general, the concentration of the nutrient should be such that no single catabolizable organic ingredient thereof is present in an amount of greater than about 1/100 of the amount of the test substrate compound included in the composition. Where the concentration of the test substrate compound is 20 millimols per liter and the nutrient concentration is such that no one catabolizable ingredient is present in an amount of more than about 0.1 millimols per liter, this provides a ratio of 1/200, which is very much on the safe side.

SPECIFIC EXAMPLE

To illustrate the invention, this example shows its use for differentiating among several species of Pseudomonas. *Pseudomonas fluorescens* can catabolize both inositol and mannitol. *Pseudomonas aeruginosa* can catabolize mannitol but not inositol. *Pseudomonas putida* can catabolize neither of these compounds. All three species can catabolize valine. Thus, the ability or inability of the species to catabolize these compounds (directly indicated by their ability or inability to effect a reduction of triphenyl tetrazolium chloride to the colored formazan compound when grown in an appropriate composition containing one of them) serves as the basis of a test to differentiate among the three Pseudomonas species.

Four compositions were prepared, all four containing: as the oxidation-reduction indicator, 0.0025% (by weight) triphenyl tetrazolium chloride; as a buffer to provide a pH of about 7, 0.7% $K_2HPO_4$, 0.3% $KH_2PO_4$, 0.01% $MgSO_4$; as a nutrient, 0.2% Proteose Peptone; as a gel former, 1.5% agar. As an alternative to the Proteose Peptone as a nutrient, there can be used the previously herein disclosed example of a nutrient composition of broad utility, the concentration being such as described in the discussion relative to the nutrient.

One composition, designated as composition A, consisted of the above with no other addition and simply served as the "negative control" to assure that none of the aforesaid ingredients could cause color formation.

To another of the compositions, designated as composition B, there was added mannitol in an amount to provide a concentration of about 20 millimols per liter.

To the third of the compositions, designated as composition C, there was added isositol in an amount to provide a concentration of about 20 millimols per liter.

To the last of the compositions, designated as composition D, there was added valine in an amount to provide a concentration of about 20 millimols per liter, this composition serving as the "positive control".

Pure liquid cultures were grown of each of the three species designated: P. fluorescens PF014; P. aeruginosa PA038; and P. putida A.3.12.

Four plates were prepared, each containing one of the four compositions and carrying the designation of the composition, i.e. plates A, B, C, and D. All four compositions were the same in color—a slightly yellowish white.

Each of the three liquid cultures was then streaked onto each of the four plates to provide isolated colonies on each of the plates.

Results: none of the three colonies on plate A, the negative control plate, caused any change in color. On plate B each of the P. fluorescens and P. aeruginosa colonies caused a change in color to red whereas the P. putida colony caused no change in color. On plate C the P. fluorescens colony caused a change in color to red whereas neither the P. aeruginosa nor the P. putida colony caused any change in color. On plate D, the positive control plate, colonies of all three species caused a change in color to red.

From the aforesaid example it will be manifest that if a culture were known to contain Pseudomonas of one or another of the three strains but with the precise strain not being known, the invention could be used to identify the precise strain. Using the compositions of the invention, as aforesaid, if the strain turned red when grown in both inositol and mannitol, it would be classified as P. fluorescens. If the strain turned red when grown in mannitol but not inositol, it would be classified as P. aeruginosa. If the strain failed to turn red when grown in either mannitol or inositol, it would be classified as P. putida.

In this specific example separate plates were used for carrying the compositions. However, as will be illustrated by the further example and discussions which follows, it is generally preferred for testing convenience and procedure that a single compartmentalized plate or other container be used, each compartment containing a different composition, in accordance with the invention, isolated from the others.

FURTHER AND MORE GENERALIZED EXAMPLE OF THE PRACTICE OF THE INVENTION

One of the classes of microorganisms quite commonly encountered in medical diagnostic, treatment and research work is Salmonella typhimurium. Also as is well known to those in the field of microbiology, there are numerous strains of Salmonella typhimurium and considerable work has already been done and is reported in the literature with respect to the catabolic behavior of each of a number of the strains. For purposes of this example of the practice of the present invention it will be assumed that the specimen to be tested and identified contains one or the other of six different strains or species of Salmonella typhimurium which will here simply be designated as Strains 1 through 6.

Strain 1 is known to catabolize d-xylose, L-rhamnose and m-tartrate, but is known not to catabolize m-inositol.

Strain 2 is known to catabolize d-xylose, m-inositol and m-tartrate, but is known not to catabolize L-rhamnose.

Strain 3 is known to catabolize d-xylose, m-inositol and L-rhamnose, but is known not to catabolize m-tartrate.

Strain 4 is known to catabolize m-inositol and L-rhamnose, but is known not to catabolize d-xylose or m-tartrate.

Strain 5 is known to catabolize d-xylose and m-tartrate, but is known not to catabolize m-inositol or L-rhamnose.

Strain 6 is known to catabolize m-inositol and m-tartrate, but is known not to catabolize d-xylose or L-rhamnose.

Hence, the four test substrate compounds to be used in the practice of the present invention for identification of the particular species of Salmonella typhimurium from amongst the six species are d-xylose, m-inositol, L-rhamnose, and m-tartrate. These test substrate compounds, and the compositions containing them, will here be designated as I, II, III, and IV, respectively, the designation V to be used for a negative control composition, i.e. a composition otherwise the same as the others except containing no test substrate compound.

The aforesaid catabolic behavior of the six species or strains is outlined in the following table:

| | Salmonella Typhimurium Catabolizes: | | | |
|---|---|---|---|---|
| Strain | I<br>d-xylose | II<br>m-inositol | III<br>L-rhamnose | IV<br>m-tartrate |
| 1 | yes | no | yes | yes |
| 2 | yes | yes | no | yes |
| 3 | yes | yes | yes | no |
| 4 | no | yes | yes | no |
| 5 | yes | no | no | yes |
| 6 | no | yes | no | yes |

In accordance with the invention five compositions are prepared, each of these compositions containing a tetrazolium compound, a buffer and a nutrient in accordance with the aforesaid teachings. More specifically, the compositions, as regards the tetrazolium compound, the buffer and the nutrient, can be the same as indicated in the previous specific example with respect to use of the invention for differentiating between species of Pseudomonas. It will be understood, of course, that as regards all ingredients other than the test substrate compound, all five compositions are identical.

Figure 2:
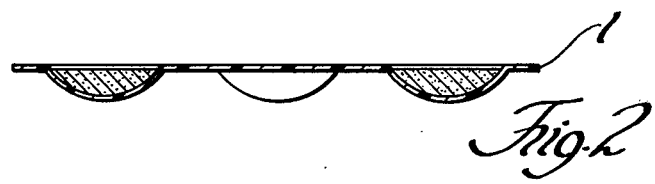
FIG. 2 is a view taken on the line 2—2 of FIG. 1.

Composition I additionally contains about 20 millimols per liter d-xylose, composition II additionally contains about 20 millimols per liter m-inositol, composition III additionally contains about 20 millimols per liter L-rhamnose and composition IV additionally contains about 20 millimols per liter m-tartrate (neutralized). Composition V is simply used as a negative control and hence contains nothing additional—contains no test substrate compound. Referring to FIGS. 1 and 2, there is shown a plate 1 which can be of any suitable material such as glass or biologically inert organic plastic, having five compartments isolated from each other and taking the form of five wells designated I-V. These five compartments I-V contain the five compositions aforesaid of like designation.

A culture of *Salmonella typhimurium* to be tested is placed in each of the five compositions and allowed to grow therein. Thereupon, identification of the particular species or strain can be made on the basis of which of the compositions remain white and which of the compositions develop a coloration (red if triphenyl tetrazolium chloride is used) in accordance with the following table:

| Strain | I | II | III | IV | V |
|---|---|---|---|---|---|
| 1 | red | white | red | red | white |
| 2 | red | red | white | red | white |
| 3 | red | red | red | white | white |
| 4 | white | red | red | white | white |
| 5 | red | white | white | red | white |
| 6 | white | red | white | red | white |

Hence, if, for example, I and IV, along with composition V, remain white whereas compositions II and III develop coloration, then the strain is identified as strain 4.

Whereas only six strains are dealt with in this example, it will be manifest that by using additional compositions, each containing a different test substrate compound, provision can be made for the possibility of other strains, it only being necessary that for each strain involved the catabolic behavior be different from all other strains with respect to some one compound or another.

While not essential, it is always preferable to use a negative control composition since if the negative control composition develops a red coloration, then the results of the total test are suspect. A positive control composition is of lesser importance though desirable where practical.

The aforesaid examples are illustrative of the use of the invention where the specimen to be tested is of known microbial content, at least to some extent. Further within the purview of the invention, however, is the use of a series of test plates, each containing a plurality of compositions distinct from each other by way of the test substrate compound included and with an early plate or plates in the series being for general, or relatively general, identification of the microorganism strain, or its catabolic behavior, and with later plates in the series being for more specific identification of the microorganism or its catabolic behavior. For example, the first test plate in the series can have compositions containing test substrate compounds which are quite different from each other and then with later plates in the series having compositions with test substrate compounds similar to each other. Alternatively, a single plate or other container having a large number—as many as hundreds—of different compositions can be used so that with but a single test a great amount of information can be gained with respect to the catabolic behavior or identification of the test specimen.

Figure 3:
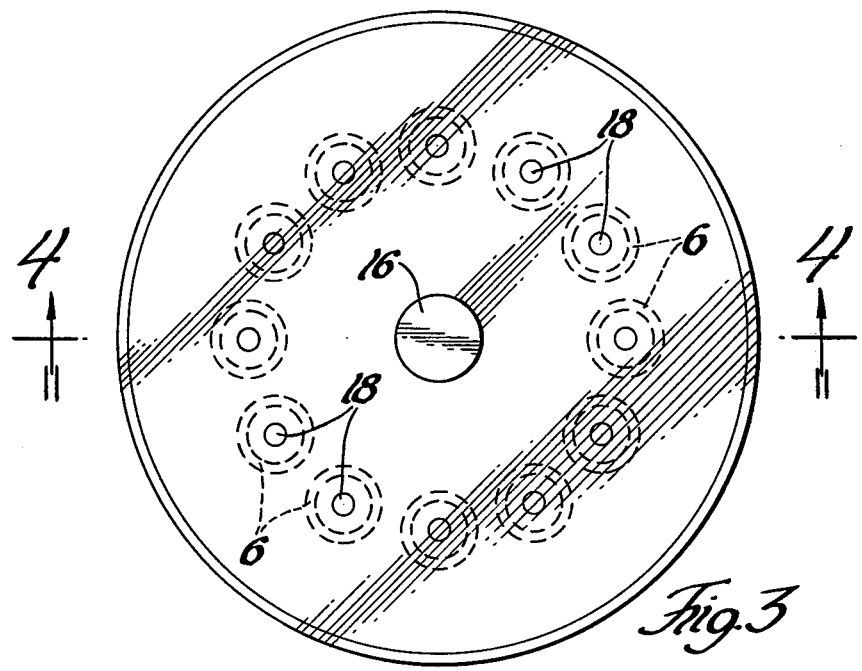
FIG. 3 is a top view of another embodiment of the invention.
Figure 4:
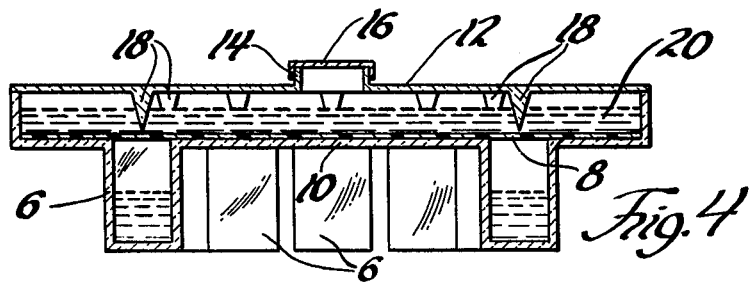
FIG. 4 is a side view in section, taken on line 4—4 of FIG. 3.

In this regard, reference is now made to FIGS. 3 and 4 which show a test container embodying, and for the convenient practice of the method of, the present invention. The container shown has a bottom portion of a molded, biologically inert, transparent organic resin having a plurality of downwardly extending compartments 6 which are isolated from each other and which, in the particular embodiment shown, are circumferentially arranged and spaced from each other. Each of the compartments 6 is partially filled with a composition which includes the oxidation-reduction indicator and a test substrate compound, in accordance with the invention, but with each composition differing from the others by way of the test substrate compound it contains. The compartments 6 are sealed from each other and from the upper part of the container by a liquid impermeable, biologically inert, organic resin membrane 8 which is sealed to the flat wall 10 which constitutes the floor of the container from which the compartments 6 extend. The upper portion of the container comprises a lid 12 of a biologically inert, relatively flexible and preferably transparent organic resin having an opening 14 sealed by a removable cap 16. The lid is further provided with a plurality of circumferentially spaced, downwardly extending pointed projections 18, each projection being immediately above one of the compartments 6. The upper portion of the container, above the membrane 8, is partially filled with an aqueous solution 20 containing nutrient and buffer for microorganism culture growth, the amount of nutrient and buffer being as taught previously herein. The cap 16 sealing the opening of the container is such as to be easily removable for introducing a specimen of the microorganism to be tested into nutrient solution 20. The membrane 8 functions as a barrier to entry of the microorganism into the compartments 6 until it is breached. That is, membrane 8 is such as to be easily punctured by the pointed projections 18 upon the application of downward pressure to the flexible lid 12. Hence, until downward pressure is applied to the lid 12, the aqueous compositions in the compartments 6 are isolated by the membrane 8 from the liquid 20 whereas after downward pressure is applied to the lid 12 so as to cause puncture of the membrane 8 by each of the projections 18, the liquid 20 can flow through the punctures into each of the compartments 6. After the puncturing the lid flexes up to its normal position. In use, the microorganism specimen to be tested is introduced into the nutrient liquid 20 by removing the cap 16 (the cap 16 being resealed after introduction of the specimen) and, after the culture is allowed to grow in the nutrient liquid, the flexible lid 12 is depressed thereby to puncture the membrane portions above each of the compartments 6 and hence allowing the culture to flow through the resulting punctures into the compartments 6 and hence into contact with each of the various compositions containing the different test substrate compounds. Since until puncture the membrane 8 seals all of the compartments 6 from each other and from nutrient liquid 20, the compositions in the compartments can be in liquid form and hence need contain no agar or other gelling agent—though agar or other gelling agent can be included if desired. The container itself can be printed with identification of the test substrate compound included in each of the compartments or alternatively, of course, the container can simply carry a numerical or the like designation for each of the compartments and be accompanied by a printed list specifying each of the various compositions. As indicated previously, it is preferable that one of the compositions be a negative control, i.e.

contain no test substrate compound. After the culture grown in the nutrient liquid is admitted to the various compartments by puncture of the membrane 8 as aforesaid, test results are indicated by the development or lack of development of color in each of the various compartments as can be easily viewed through the transparent container. If desired, nutrient and buffer can be initially included in the compositions in the compartments, or the supply of these ingredients can be solely by way of the aqueous nutrient and buffer solution 20 in the upper part of the container. It will, however, be understood that, in any case, at the time of culture growth in the compartments the compositions in the compartments do contain all four of the essential ingredients for the test, as herein taught, save only for the negative control composition (if one is used) which does not contain test substrate compound.

Hence, it will be understood that whereas the invention has been described in its particulars by reference to various preferred embodiments thereof, various changes and modifications may be made all within the full and intended scope of the claims which follow.

What is claimed is:

1. A composition for identifying or testing a microorganism by growing a culture of the microorganism in contact therewith, said composition consisting essentially of an aqueous solution containing: (1) an oxidation-reduction indicator which substantially irreversibly undergoes a change in color upon being reduced; (2) a biodegradable test substrate compound which, when catabolized by a microorganism, will engender a reduction of said indicator; (3) a buffer to maintain the pH of the composition at a level which enables microorganism culture growth without engendering or preventing reduction of said indicator; and (4) a microorganism nutrient in a concentration sufficient to support microorganism culture growth without engendering reduction of said indicator.

2. A composition as set forth in claim 1 wherein said oxidation-reduction indicator is present in an amount of from about 0.0001% to 0.1% by weight, wherein said test substrate compound is present in an amount of at least about 2 millimoles per liter, wherein the buffer maintains the pH of the composition at from about 4.5 to 12.5, and wherein the concentration of the nutrient is such that no one catabolizable ingredient thereof is present in an amount greater than one millimole per liter.

3. A composition as set forth in claim 2 wherein said tetrazolium compound is triphenyl tetrazolium chloride.

4. A composition as set forth in claim 3 wherein said triphenyl tetrazolium chloride is present in an amount of about 0.0025% by weight.

5. A composition as set forth in claim 2 wherein the number of millimoles of test substrate compound present in the composition is at least 100 times greater than the number of millimoles of any one catabolizable ingredient of said nutrient.

6. A composition as set forth in claim 5 wherein the test substrate compound is present in an amount of about 20 millimoles per liter and wherein the concentration of the nutrient is such that the amount of each catabolizable ingredient thereof is about 0.1 millimole per liter.

7. A composition as set forth in claim 1 wherein there is also present a non-biodegradable gel former to cause such composition to have a gel-like consistency.

8. A composition as set forth in claim 1 wherein said oxidation-reduction indicator is a tetrazolium compound which undergoes a change in color when reduced to a formazan compound and wherein said test substrate compound when catabolized by a microorganism engenders a reduction of said tetrazolium compound to a formazan compound.

9. A composition for identifying or testing a microorganism by growing a culture of the microorganism in contact therewith, said composition consisting essentially of an aqueous solution containing: (1) from about 0.0001% to 0.1% by weight of a tetrazolium compound which undergoes a substantially irreversible change in color upon being reduced to a formazan compound, (2) from about 2 to 500 millimoles per liter of a biodegradable test substrate compound which, when catabolized by a microorganism, will engender reduction of the tetrazolium compound to a formazan compound, (3) a buffer in an amount sufficient to maintain the pH of the composition at a level which is within the range of 4.5 to 12.5 and which enables microorganism culture growth without engendering or preventing reduction of the tetrazolium compound to a formazan compound, and (4) a microorganism nutrient in a concentration such that no one catabolizable ingredient thereof is present in an amount greater than one millimole per liter or greater than 1/100 the amount of the test substrate compound.

10. A method for identifying or testing a microorganism comprising growing a culture of the microorganism in contact with each of a plurality of compositions each consisting essentially of an aqueous solution containing: (1) an oxidation-reduction indicator which substantially irreversibly undergoes a change in color upon being reduced, (2) a biodegradable test substrate compound which, when catabolized by a microorganism, will engender reduction of said indicator, (3) a buffer to maintain the pH of the composition at a level which enables microorganism culture growth without engendering or preventing reduction of said indicator, and (4) a microorganism nutrient in a concentration sufficient to support microorganism culture growth without engendering reduction of said indicator, the test substrate in each of said compositions being different than the test substrate in each of the other compositions, said compositions being otherwise substantially identical to each other.

11. A method as set forth in claim 10 wherein said oxidation-reduction indicator is present in an amount of from about 0.0001% to 0.1% by weight, wherein said test substrate compound is present in an amount of at least about 2 millimoles per liter, wherein the buffer maintains the pH of the composition at from about 4.5 to 12.5, and wherein the concentration of the nutrient is such that no one catabolizable ingredient thereof is present in an amount greater than 1 millimole per liter.

12. A method as set forth in claim 11 wherein said tetrazolium compound is triphenyl tetrazolium chloride.

13. A method as set forth in claim 12 wherein said triphenyl tetrazolium chloride is present in an amount of about 0.0025% by weight.

14. A method as set forth in claim 11 wherein the number of millimoles of test substrate compound present in the composition is at least 100 times greater than the number of millimoles of any one catabolizable ingredient of said nutrient.

15. A method as set forth in claim 14 wherein the test substrate compound is present in an amount of about 20 millimoles per liter and wherein the concentration of the nutrient is such that the amount of each catabolizable ingredient thereof is about 0.1 millimole per liter.

16. A method as set forth in claim 10 wherein there is also present a biologically and chemically inert gel former to cause such composition to have a gel-like consistency.

17. A method as set forth in claim 10 wherein said oxidation-reduction indicator is a tetrazolium compound which undergoes a change in color when reduced to a formazan compound and wherein said test substrate compound, when catabolized by a microorganism, engenders a reduction of said tetrazolium compound to a formazan compound.

18. A device for identifying or testing a microorganism comprising a container having a separate compartments, each of a plurality of said compartments having therein a composition consisting essentially of an aqueous solution containing (1) an oxidation-reduction indicator which substantially irreversibly undergoes a change in color upon being reduced, (2) a biodegradable test substrate compound which, when catabolized by a microorganism, will engender reduction of said indicator, (3) a buffer to maintain the pH of the composition at a level which enables microorganism culture growth without engendering or preventing reduction of said indicator and (4) a microorganism nutrient in a concentration sufficient to support microorganism culture growth without engendering reduction of said indicator, the composition in each of said plurality of compartments containing a different test substrate compound than that in the compositions in the other of said plurality of compartments but the compositions in all of said plurality of compartments being otherwise substantially identical.

19. A device as set forth in claim 18 wherein said container also has a separate compartment which has therein a composition which contains no test substrate compound but which is otherwise substantially identical to the compositions in the other compartments.

20. A device as set forth in claim 18 wherein the composition in each compartment of said container additionally contains a non-biodegradable gel former whereby each of said compositions has a gel-like consistency.

21. A device as set forth in claim 18 wherein said oxidation-reduction indicator is present in each of said compositions in an amount of from about 0.0001% to 0.1% by weight, said test substrate compound is present in each of said compositions in an amount of at least about 2 millimoles per liter, said buffer is present in each of said compositions in an amount to maintain the pH at from about 4.5 to 12.5, and the concentration of the nutrient in each of said compositions is such that no one catabolizable ingredient thereof is present in an amount greater than one millimole per liter.

22. A device as set forth in claim 21 wherein the number of millimoles of test substrate compound present is at least 100 times greater than the number of millimoles of any one catabolizable ingredient of said nutrient.

23. A device as set forth in claim 22 wherein the test substrate compound is present in an amount of about 20 millimoles per liter and the concentration of the nutrient is such that the amount of each catabolizable ingredient thereof is about 0.1 millimole per liter.

24. A device as set forth in claim 18 wherein, in the composition in each of said compartments, said oxidation-reduction indicator is a tetrazolium compound which undergoes a change in color when reduced to a formazan compound.

25. A composition as set forth in claim 24 wherein, in the composition in each of said compartments, said tetrazolium compound is triphenyl tetrazolium chloride.

26. A device as set forth in claim 25 wherein, in the composition in each of said compartments, said triphenyl tetrazolium chloride is present in an amount of about 0.0025% by weight.

27. A device for identifying or testing a microorganism comprising a container having an upper portion containing a nutrient solution and adapted to receive a microorganism culture for growth therein, and a lower portion having a plurality of separate compartments each of which is separated from said upper portion by a barrier which is liquid impermeable but which is breachable to allow said solution with a microorganism culture therein to flow into said compartments, each of said compartments having therein a composition containing an oxidation-reduction indicator which undergoes a change in color upon being reduced and biodegradable test substrate compound which, when catabolized by a microorganism, engenders reduction of said indicator, the composition in each of said compartments containing a different test substrate compound than that in the compositions in the other of said compartments and the concentration of said nutrient in said nutrient solution being sufficient to support microorganism culture growth without engendering reduction of said indicator when said nutrient solution with a microorganism culture therein comes into contact with the compositions in said compartments.

28. A device as set forth in claim 27 wherein said barrier is a membrane and wherein said container includes means for puncturing said membrane.

29. A method for identifying or testing a microorganism comprising growing a culture of the microorganism in a nutrient solution and then bringing said nutrient solution with the microorganism culture therein into contact with each of a plurality of compositions each of which consists essentially of an aqueous solution containing an oxidation-reduction indicator which substantially irreversibly undergoes a change in color upon being reduced, and a biodegradable test substrate compound which, when catabolized by a microorganism, will engender reduction of the indicator, the test substrate compound in each of said compositions being different than the test substrate compound in each of the other of the compositions and the concentration of the nutrient in said nutrient solution being sufficient to support microorganism culture growth without engendering reduction of the indicator when said nutrient solution with the microorganism culture therein contacts said compositions.

* * * * *